United States Patent [19]

Chajuss

[11] Patent Number: 5,871,743
[45] Date of Patent: Feb. 16, 1999

[54] TOPICAL APPLICATION OF SOY MOLASSES

[76] Inventor: Daniel Chajuss, Misgav Dov 29, Mobile Post Emek Sorek 76867, Israel

[21] Appl. No.: 959,322

[22] Filed: Oct. 28, 1997

[30] Foreign Application Priority Data

Oct. 31, 1996 [IL] Israel ......................................... 119535

[51] Int. Cl.⁶ ............................. A61K 35/78; A61K 7/48
[52] U.S. Cl. ..................... 424/195.1; 424/70.1; 424/401; 514/844; 514/846; 514/852; 514/858; 514/859; 514/944
[58] Field of Search ..................................... 424/401, 70.1, 424/195.1; 514/844–846, 852, 944, 858, 559

[56] References Cited

U.S. PATENT DOCUMENTS 5,635,186  6/1997  Bathurst et al. ..................... 424/195.1

*Primary Examiner*—Jyothsna Venkat
*Attorney, Agent, or Firm*—Dennison, Meserole, Pollack & Scheiner

[57] ABSTRACT

A topical composition comprising soy molasses extract containing soy phytochemicals, useful in the treatment and amelioration of dermatologic disorders and for cosmetic purposes when applied topically.

7 Claims, No Drawings

5,871,743

TOPICAL APPLICATION OF SOY MOLASSES

FIELD OF THE INVENTION

The present invention relates to a topical composition of soy molasses and its therapeutic application.

BACKGROUND OF THE INVENTION

Soy molasses is an aqueous alcohol soybean solubles extract made commercially essentially as disclosed in my Israel Patent No. 19168. The aqueous alcohol extraction is preferably conducted on defatted soybean material, such as non-toasted defatted soybean flakes, with warm aqueous alcohol such as methanol, ethanol, or isopropanol. The alcohol and some of the water, is then removed. This can be done by evaporation, distillation, steam stripping, elution, column separation, membrane separation or other techniques known per se, to obtain essentially alcohol free soy molasses having a desired moisture content. In Israel Patent Applications Nos. 115110 and 119107, I disclose a novel therapeutic use of soy molasses and modified soy molasses, when taken orally, as a composite source of various soy phytochemicals to prevent and ameliorate diverse and various pathological conditions. Soy molasses being virtually a concentrated composite source of substantially all the soy phytochemicals, these Patent Applications describe methods and ways by which the soy molasses can be taken orally. These Patent Applications however do not teach nor suggest that soy molasses can be used in topical applications to prevent and ameliorate various dermatologic disorders and in cosmetics.

The present application is based on our surprising and unexpected discovery that soy molasses can be highly useful to provide soy phytochemicals, not only when taken orally, thus being effective internally, but that it is also highly effective in topical applications in the prevention, treatment and amelioration of various dermatologic disorders and for cosmetic use. Since soy molasses is used because of its phytochemicals composition, the designation "soy molasses" includes for the purpose of this invention soy molasses that is modified by the removal from it of certain components, especially of components that are not considered phytochemicals, such as soy sugars. The present patent also includes for the purpose of this invention derivatives of soy molasses, that can serve as a source of soy molasses phytochemicals.

It is the object of the present invention to provide a topical composition of soy molasses, providing an inexpensive composite source of soybean phytochemical constituents.

Another object of the invention is to provide topical preparations based on soy molasses, for treatment and amelioration of pathological dermatologic conditions and for cosmetic use.

Another object of the invention is to provide a cosmetic composition containing soy molasses.

Yet another object of our invention is to provide a method of treatment and amelioration of dermatologic disorders by applying a topical composition containing soy molasses.

SUMMARY OF THE INVENTION

The present invention provides topical compositions containing soy molasses, and optionally additional active and/or inert ingredients. These compositions may be in the form of ointments, creams, lotions, gels, balms, cleansing emulsions, liquid and dry soaps, shampoos, solutions, etc., providing soy phytochemicals useful in treatment and amelioration of various dermatologic disorders and in cosmetics.

DETAILED DESCRIPTION OF THE INVENTION

The present patent application is a further development of the Israel Patent Applications Nos. 115110 and 119107, which disclose the novel internal therapeutic effect of soy molasses, when taken orally, because of its phytochemicals content. The principal phytochemicals of the soy molasses are the phytoestrogens isoflavones, the Bowman-Birk group of trypsin and chymotrypsin inhibitors (BBI), phenolic acids, saponins, phytates, phospholipids and phytosterols. Soy molasses can consequently be considered as an enriched composite source of soybean phytochemical components that are highly beneficial for prevention, treatment and amelioration of various pathological conditions when taken orally.

While the Israel Patent Applications Nos. 115110 and 119107 describe the modes and ways by which the soy molasses can be taken orally, they do not teach or suggest topical application of soy molasses or modified soy molasses for treatment and amelioration of various dermatologic disorders or for cosmetic purposes.

The present invention is based on our discovery that soy molasses can be utilized for topical applications as well. Thus, soy molasses with or without additional inert and/or active ingredients, can be formulated into topical compositions. These compositions may contain in addition to soy molasses, drugs or other physically active ingredients, colorants, perfumes, essences, fillers, binders, preservatives, etcetera, known for use in preparations. These compositions may be in the form of ointments, creams, lotions, gels, balms, cleansing emulsions, liquid and dry soaps, shampoos, solutions, etcetera, which provide an external accessible source of soy phytochemicals to prevent, treat and ameliorate dermatologic disorders, as well as for cosmetic purposes.

The mode of action of the soy molasses is postulated to be its unique and enriched phytochemical content made up of isoflavones, Bowman-Birk trypsin and chymotrypsin inhibitors (BBI), phenolic acids, saponins, phytosterols, phospholipids, phytates, etcetera, which may have a synergetic and highly favorable effect, acting as estrogen antagonists and as anti-androgens, reducing the proliferation of harmful cells and having anti-oxidant, anti-microbial, anti-fungus and anti-viral activities. The soy molasses phytochemicals are apparently able to block inflammatory responses, act as signal interceptor and thus able to ameliorate conditions resulting from aberrations in signalling pathways.

The present invention will be further illustrated and clarified by the following examples:

EXAMPLE I

One part by weight of soy molasses dehydrated and micromilled to a very fine powder and one part by weight of a moisturizer cream ("All Purpose Cream" made by CTS Novis, Israel), were thoroughly mixed in a high speed blender to obtain a modified homogenous, soy molasses moisturizer cream mixture. This moisturizer cream was topically applied daily to dermatophyte infection afflicted areas of the feet (*Tinea pedis*) in three volunteers with an athlete's foot infection. After one to three days of application a nearly complete cure was observed in all the treated cases. No side effects were observed.

EXAMPLE II

One part by weight of soy molasses dehydrated and micromilled to a very fine powder and one part by weight of a moisturizer ("Delicate Rich Moisturizer" made by Gigi Laboratories, Israel), were thoroughly mixed in a high speed blender to obtain a modified homogenous, soy molasses moisturizer mixture. This moisturizer mixture was topically applied daily to acne afflicted areas of two volunteers with mild to moderate acne. After one to three days of application, marked improvement was noticed. Within twelve days of application nearly a complete cure was observed in the treated cases. The acne comedones, skin lesions, pustules, papules and acne cysts almost totally disappeared. No side effects were observed.

EXAMPLE III

One part by weight of soy molasses dehydrated and micromilled to a very fine powder and one part by weight of a shampoo ("pH 5.5" made by Johnson & Johnson, Greece), were thoroughly mixed in a high speed blender to form a homogenous soy molasses-shampoo mixture. This mixture was applied as a shampoo by a volunteer with dandruff problems and mild seborrheic dermatitis and was allowed to remain on the scalp for about ten minutes before rinsing with water. After several days of treatment, once a day, with the shampoo mixture, a reduction of dandruff scaling of the scalp was observed. Strengthening of the hair, less hair losses and more luster of the hair were claimed by all users. No adverse side effects were observed.

EXAMPLE IV

Soy molasses dehydrated and micromilled, was mixed and homogenized with a finely milled soap at one to nine ratio of the micromilled soy molasses powder to the milled soap powder. The mixture was heated, and remolded into soap bars with temperature and moisture adjustment. The new soap bars containing soy molasses solids had an increased amount of fine stabilized foam. When tested by a panel of users in comparison with the corresponding original soy molasses free soap, better cleansing effects with softer and more velvety skin were reported by the panel. No adverse effects were noted.

There is an almost infinite number of variations and modes to provide for soy molasses, or derivatives thereof, that can have topical application alone, in a different dry matter concentrations, or as compounded preparations of ointments, lotions, creams, gels, cleansing emulsions, liquid and dry soaps, balms, shampoos, solutions, etcetera, to provide an externally accessible source of the different soy molasses phytochemicals for treatment and amelioration of various dermatologic disorders, cosmetic environment and appearances. This without departing from the spirit of the invention, on condition that the fundamental principle of the employment of soy molasses as set forth above is followed.

What is claimed is:

1. A method for treating an area affected with acne, athlete's foot or dandruff comprising applying to the affected area a topical composition comprising a homogeneous blend of a topical base formulation and soy molasses containing soy phytochemicals.

2. A method in accordance with claim 1, wherein the soy phytochemicals comprise phytoestrogens, isoflavones, Bowman-Birk Inhibitors (BBI), phenolic acids, saponins, phytates, phospholipids and phytosterols.

3. A method in accordance with claim 1, wherein the composition comprises a cream.

4. A method in accordance with claim 1, wherein the composition comprises a lotion.

5. A method in accordance with claim 1, wherein the composition comprises a shampoo.

6. A method in accordance with claim 1, wherein the composition comprises a soap.

7. A method in accordance with claim 1, wherein the composition comprises a gel.

* * * * *